US006194640B1

(12) United States Patent
Slabas et al.

(10) Patent No.: US 6,194,640 B1
(45) Date of Patent: Feb. 27, 2001

(54) PLANT EXPRESSING 2-ACYLTRANSFERASE

(75) Inventors: Antoni Ryszard Slabas, High Shincliffe; Adrian Paul Brown, Shadforth, both of (GB)

(73) Assignee: Biogemma UK Limited, Cambridge (GB)

( * ) Notice: Subject to any disclaimer, the term of this patent is extended or adjusted under 35 U.S.C. 154(b) by 0 days.

(21) Appl. No.: 09/035,098

(22) Filed: Mar. 5, 1998

Related U.S. Application Data

(62) Division of application No. 08/454,267, filed as application No. PCT/GB93/02528 on Dec. 10, 1992, now Pat. No. 5,843,739.

(30) Foreign Application Priority Data

Dec. 10, 1992 (GB) .................................................. 9225845

(51) Int. Cl.[7] ....................................................... H01H 5/00

(52) U.S. Cl. .......................... 800/306; 800/295; 800/278

(58) Field of Search ............................ 435/410; 800/228, 800/306, 295

(56) References Cited

U.S. PATENT DOCUMENTS

| | | | |
|---|---|---|---|
| 5,843,739 | 12/1998 | Slabas et al. | 435/172.3 |
| 5,945,323 | 8/1999 | Slabas et al. | 435/193 |

FOREIGN PATENT DOCUMENTS

| | | |
|---|---|---|
| 0 116 718 A1 | 8/1984 | (EP) . |
| 0 242 246 A1 | 10/1987 | (EP) . |
| 0 270 822 A1 | 6/1988 | (EP) . |
| 0 344 029 A1 | 11/1989 | (EP) . |
| WO 92/13082 | 8/1992 | (WO) . |

OTHER PUBLICATIONS

International Search Report from International Application No. PCT/GB93/02528.

Bernerth, R. and M. Frentzen, "Utilization of Erucoyl–CoA by Acyltransferases from Developing Seeds of *Brassica napus* (L. ) Involved in Triacylglycerol Biosynthesis," *Plant Sci* . 67:21–28 (1990).

Bernerth et al., "Utilization of erucoyl–CoA by acetyltransferases from developing seeds of Brassica napus (L.) involved in triacylglycerol biosynthesis," *Chemical Abstracts 113*(3):20895a (1990).

Cao, Y.–Z. and A.H.C. Huang, "Diacylglycerol Acyltransferase in Maturing Oil Seeds of Maize and Other Species," *Plant Physiol. 82* :813–820 (1986).

Cao, Y. et al., "Lysophosphatidate Acyltransferase in the Microsomes from Maturing Seeds of Meadowfoam (*Limnanthes alba* )," *Plant Physiol. 94*:1199–1206 (1990).

Coleman J., "Characterization of the *Escherichia coli* gene for 1–acyl–sn–glycerol–3–phosphate acyltransferase (plsC)," *Mol. Gen. Genet. 232*:295–303 (Mar. 1992).

Hares, W. and M. Frentzen, "Substrate specificities of the membrane–bound and partially purified microsomal acyl–CoA:1–acylglycerol–3–phosphate acyltransferase from etiolated shoots of *Pisum savatium* (L.)," *Chemical Abstracts 115*:201740h (Nov. 1991).

Hares, W. and M. Frentzen, "Substrate specificites of the membrane–bound and partially purified microsomal acyl–CoA:1–acylglycerol–3–phosphate acyltransferase from etiolated shoots of *Pisum sativum* (L.)," *Planta 185*:124–131 (Aug. 1991).

Herrera–Estrella, L. et al., "Chimeric genes as dominant selectable markers in plant cells," *Embo J. 2*(6):987–995 (1983).

Herrera–Estrella, L. et al., "Expression of chimaeric genes transferred into plant cells using a Ti–plasmid–derived–vector," *Nature 303*:209–213 (1983).

Knauf V.C., "The application of genetic engineering to oilseed crops," *Trends in Biotechnology 5*:40–47 (1987).

Loehden, I. et al., "Acyl–CoA:1–acylglycerol–3–phosphate acyltransferase from developing seeds of Limnanthes douglasii (R.Br.) and Brassica napus (L.)," *Chemical Abstracts 116*(9):79057u (Mar. 1992).

Löhden, I. et al., "Acyl–CoA: 1–acylglycerol–3–phosphate acyltransferase from developing seeds of *Limnanthes douglasii* (R. Br.) and *Brassica napus* (L.)," in: Plant Lipid Biochemistry, Structure and Utilization: Proc. 9th Int. Symp. Plant Lipids, Quinn, P.J. and J.L. Harwood, eds., pp. 175–177 (1990).

Murata, N. et al., "Genetically engineered alteration in the chilling sensitivity of plants," *Nature 356* :710–713 (Apr. 1992).

Oo, K.C. and A.H.C. Huang, "Lysophosphatidate Acyltransferase Activities in the Microsomes from Palm Endosperm, Maize Scutellum, and Rapeseed Cotyledon of Maturing Seeds," *Plant Physiol 91:*1288–1295 (1989).

Peterek, G. et al., "Approaches of cloning the 1–acylglycerol–3–phosphate acyltransferase," 8th Workshop on Plant Lipids, 90th Conference of the Gesellschaft für Biologische Chemie, *Biol. Chem. Hoppe–Seyler 372*(8):539 (Aug. 1991).

Peterek, G. et al., "Wege zur Klonierung der 1 Acetylgycerin–3–Phosphat–Acyltransferase," 47th Annual Meeting of the German Society for Fat Science, *Fat Science Technology 93*(11):417–418 (Nov. 1991).

(List continued on next page.)

*Primary Examiner*—Charles L. Patterson, Jr.
(74) *Attorney, Agent, or Firm*—Sterne, Kessler, Goldstein & Fox, P.L.L.C.

(57) ABSTRACT

Plants, particularly transgenic plants, maybe produced having a 2-acyltransferase enzyme or other insoluble acyltransferase enzyme with an altered substrate specificity compared to the native enzyme. For example, oil seed rape (*Brassica napus*) may contain a 2-acyltransferase transgene derived from *Limnanthes douglassi* in order to increase the erucic acid content of the oil. The cDNA sequence of maize (*Zea mays*) 2-acyltransferase is disclosed and is useful for cloning acyltransferase genes and/or CDNAs from other organisms, including *L. douglassi.*

31 Claims, 8 Drawing Sheets

OTHER PUBLICATIONS

Studier, F.W. et al., "Use of T7 RNA Polymerase to Direct Expression of Cloned Genes," *Methods in Enzymology 185:*60–89 (1990).

Wolter, V.F.P. et al., "Biochemische und molekularbiologische Ansätze zur Veränderung der Fettsäurezusammensetzung des Rapsöls," *Fat Sci. Technol. 93*(8):288–290 (Aug. 1991).

Unverified English translation of Wolter, V.F.P. et al., "Biochemische und molekularbiologische Ansätze zur Veränderung der Fettsäurezusammensetzung des Rapsöls," *Fat Sci. Technol. 93*(8):288–290 (Aug. 1991).

```
1/1                                     31/11
CCC CGT CCT CCT CGT CGC CGG CGG AGC CGC CTA CTA TCG CCT GGA GAA GGA GCG CCG CGG
P   R   P   P   R   R   R   R   S   R   L   L   S   P   G   E   G   A   P   R
61/21                                   91/31
GGA GCT TTT CCC ACT GCC GAC TGC CGT CTG ACC CTC CGA GAT CGG AAG CGG CGC CGG CGC
G   A   F   P   T   A   D   C   R   L   T   L   R   D   R   K   R   R   R   R
121/41                                  151/51
CGG CCG GCG ATG GCG ATC CCG CTC GTG CTC GTC GTG CTC CCG CTC GGC CTG CTC TTC CTC
R   P   A   M   A   I   P   L   V   L   V   V   L   P   L   G   L   L   F   L
181/61                                  211/71
CTG TCC GGC CTC ATC GTC AAC GCC ATC CAG GCC GTC CTA TTT GTG ACG ATA AGG CCC TTT
L   S   G   L   I   V   N   A   I   Q   A   V   L   F   V   T   I   R   P   F
241/81                                  271/91
TCG AAG AGC TTC TAC CGT CGG ATC AAC AGA TTC TTG GCC GAG CTG CTG TGG CTT CAG CTT
S   K   S   F   Y   R   R   I   N   R   F   L   A   E   L   L   W   L   Q   L
301/101                                 331/111
GTC TGG GTG GTG GAC TGG TGG GCA GGT GTT AAG GTA CAA CTG CAT GCA GAT GAG GAA ACT
V   W   V   V   D   W   W   A   G   V   K   V   Q   L   H   A   D   E   E   T
361/121                                 391/131
TAC AGA TCA ATG GGT AAA GAG CAT GCA CTC ATC ATA TCA AAT CAT CGG AGT GAT ATT GAT
Y   R   S   M   G   K   E   H   A   L   I   I   S   N   H   R   S   D   I   D
421/141                                 451/151
TGG CTC ATT GGA TGG ATA TTG GCC CAG CGT TCA GGG TGC CTT GGA AGT ACA CTT GCT GTC
W   L   I   G   W   I   L   A   Q   R   S   G   C   L   G   S   T   L   A   V
481/161                                 511/171
ATG AAG AAG TCA TCC AAG TTC CTT CCA GTT ATT GGC TGG TCA ATG TGG TTT GCA GAG TAC
M   K   K   S   S   K   F   L   P   V   I   G   W   S   M   W   F   A   E   Y
541/181                                 571/191
CTC TTT TTG GAA AGG AGC TGG GCC AAG GAT GAA AAG ACA CTA AAG TGG GGT CTC CAA AGG
L   F   L   E   R   S   W   A   K   D   E   K   T   L   K   W   G   L   Q   R
```

FIG. 1A

```
601/201                                 631/211
TTG AAA GAC TTC CCT AGA CCA TTT TGG CTA GCT CTT TTC GTC GAG GGT ACT CGC TTT ACT
L   K   D   F   P   R   P   F   W   L   A   L   F   V   E   G   T   R   F   T
661/221                                 691/231
CCA GCA AAG CTT CTC GCA GCT CAG GAA TAT GCG GCC TCC CAG GGC TTA CCG GCT CCT AGA
P   A   K   L   L   A   A   Q   E   Y   A   A   S   Q   G   L   P   A   P   R
721/241                                 751/251
AAT GTA CTT ATT CCA CGT ACC AAG GGA TTT GTA TCT GCT GTA AGT ATT ATG CGA GAT TTT
N   V   L   I   P   R   T   K   G   F   V   S   A   V   S   I   M   R   D   F
781/261                                 811/271
GTT CCA GCC ATT TAT GAT ACA ACT GTA ATA GTC CCT AAA GAT TCC CCT CAA CCA ACA ATG
V   P   A   I   Y   D   T   T   V   I   V   P   K   D   S   P   Q   P   T   M
841/281                                 871/291
CTG CGG ATT TTG AAA GGG CAA TCA TCA GTG ATA CAT GTC CGC ATG AAA CGT CAT GCA ATG
L   R   I   L   K   G   Q   S   S   V   I   H   V   R   M   K   R   H   A   M
901/301                                 931/311
AGT GAG ATG CCA AAA TCA GAT GAG GAT GTT TCA AAA TGG TGT AAA GAC ATT TTT GTG GCA
S   E   M   P   K   S   D   E   D   V   S   K   W   C   K   D   I   F   V   A
961/321                                 991/331
AAG GAT GCC TTA CTG GAC AAG CAT TTG GCA ACA GGC ACT TTC GAT GAG GAG ATT AGA CCT
K   D   A   L   L   D   K   H   L   A   T   G   T   F   D   E   E   I   R   P
1021/341                                1051/351
ATT GGC CGT CCA GTG AAA TCA TTG CTG GTG ACC CTG TTC TGG TCG TGC CTC CTG CTG TTT
I   G   R   P   V   K   S   L   L   V   T   L   F   W   S   C   L   L   L   F
1081/361                                1111/371
GGC GCC ATC GAG TTC TTC AAG TGG ACA CAG CTT CTG TCG ACG TGG AGG GGT GTG GCG TTC
G   A   I   E   F   F   K   W   T   Q   L   L   S   T   W   R   G   V   A   F
```

FIG. 1B

```
1141/381                                1171/391
ACT GCC GCA GGG ATG GCG CTT GTG ACG GGT GTC ATG CAT GTC TTC ATC ATG TTC TCC CAG
T   A   A   G   M   A   L   V   T   G   V   M   H   V   F   I   M   F   S   Q
1201/401                                1231/411
GCT GAG CGG TCG AGC TCA GCC AGG GCG GCA CGG AAC CGG GTC AAG AAG GAA TGA AAA ATG
A   E   R   S   S   S   A   R   A   A   R   N   R   V   K   K   E   *   K   M
1261/421                                1291/431
GAG GGT GGA GAT GAG GTT CTC GTG GGG TTT GTT ATG GGC AAC CTT CAA AAG GAC TCT CCA
E   G   G   D   E   V   L   V   G   F   V   M   G   N   L   Q   K   D   S   P
1321/441                                1351/451
TTC ATA TTA GTA TTA ATT CAT ATA TAT GCA GCG CCA AAT TCC AGA CAT TGA TAT GCT CTC
F   I   L   V   L   I   H   I   Y   A   A   P   N   S   R   H   *   Y   A   L
1381/461                                1411/471
AAA TAG GAT GTT CTG CTC CCC TCT TGT ATT TGT ATG CAG GAA AGG GTT TGT AGG GAG TTT
K   *   D   V   L   L   P   S   C   I   C   M   Q   E   R   V   C   R   E   F
1441/481                                1471/491
ACC CCC CCC CCC CCC CCC CCC GCC TTT CTT TGG GgA AGA AAG AcA TaT TCT GGA AGC CTT
T   P   P   P   P   P   P   A   F   L   W   G   R   K   T   Y   S   G   S   L
1501/501
CCA GTA GTt CAA AA
P   V   V   Q
```

FIG. 1C

```
plsB  - Y F V E G G R S R T G R L L D -
          : : : : : :   : :     : :
plsC  - M F P E G T R S R G R G L L P -
          : : : : : :           : :
maize - L F V E G T R F T P A K L L A -
          * + * * + * + +       * *
```

FIG.2 mutant
JC201 mutant +
pPLSC mutant +
maize
cDNA

```
Maize = 374 aa vs.rape = 311 aa

51.5% identity;   Optimized score: 705

                10        20        30        40        50        60
maize   MAIPLVLVVLPLGLLFLLSGLIVNAIQAVLFVTIRPFSKSFYRRINRFLAELLWLQLVWV
        ::.. . :..:::.::..:::.::
rape    MAMA-AAVIVPLGILFFISGLVVN------------------------------------
                 10        20

                70        80        90       100       110       120
maize   VDWWAGVKVQLHADEETYRSMGKEHALIISNHRSDIDWLIGWILAQRSGCLGSTLAVMKK
                                                   : ::::::::.::::::
rape    -------------------------------------------LLQRSGCLGSALAVMKK
                                                        30        40

               130       140       150       160       170       180
maize   SSKFLPVIGWSMWFAEYLFLERSWAKDEKTLKWGLQRLKDFPRPFWLALFVEGTRFTPAK
        ::::::::::::::.:::::::.:::::.::: :::::.:::::::::::::::::: ::
rape    SSKFLPVIGWSMWFSEYLFLERNWAKDESTLKSGLQRLNDFPRPFWLALFVEGTRFTEAK
                50        60        70        80        90       100
```

FIG. 5A

```
                 190       200       210       220       230       240
maize   LLAAQEYAASQGLPAPRNVLIPRTKGFVSAVSIMRDFVPAIYDTTVIVPKDSPQPTMLRI
        : :::::::: .::.:::::::::::::::::: ::.::::::: :: .::.::.:::::.
rape    LKAAQEYAASSELPVPRNVLIPRTKGFVSAVSNMRSFVPAIYDMTVAIPKTSPPPTMLRL
                 110       120       130       140       150       160

                 250       260       270       280       290
maize   LKGQSSVIHVRMKRHAMSEMPKSDEDVSKWCKDIFVAKDALLDKHLATGTF-DEEIRPIG
        .:::.::.:::..: :.:...:.:......::.: ::.:::::::::.:..:: ... . ::
rape    FKGQPSVVHVHIKCHSMKDLPESEDEIAQWCRDQFVTKDALLDKHIAADTFAGQKEQNIG
                 170       180       190       200       210       220

        300       310       320       330       340       350
maize   RPVKSLLVTLFWSCLLLFGAIEFFKWTQLLSTWRGVAFTAAGMALVTGVMHVFIMFSQAE
        ::.::: :.: :.::: .::.:.:.:.:.:.:.:.:..: :....:  :...:. ::.:
rape    RPIKSLAVVLSWACLLTLGAMKFLHWSNLFSSWKGIALSALGLGIITLCMQILIRSSQSE
                 230       240       250       260       270       280

        360       370
maize   RSSSARAARNRVKKE
        ::..:..:... :..
rape    RSTPAKVAPAKPKDN
                 290
```

FIG. 5B

PLANT EXPRESSING 2-ACYLTRANSFERASE

CROSS-REFERENCE TO RELATED APPLICATIONS

This application is a divisional of Appl. Ser. No. 08/454,267 filed on Aug. 4, 1995 and now U.S. Pat. No. 5,843,739, which is the U.S. National Phase of International Appl. No. PCT/GB93/02528, international filing date Dec. 10, 1992.

FIELD OF THE INVENTION

This invention relates to modified plants. In particular, the invention relates to plants modified such that at least part of the plant (for example seeds of the plant) is capable of yielding a commercially useful oil.

BACKGROUND OF THE INVENTION

Plants have long been a commercially valuable source of oil. Nutritional uses of plant-derived oils have hitherto been dominant, but attention is now turning additionally to plants as a source of industrially useful oils, for example as replacements for or improvements on mineral oils. Oil seeds, such as from rape, have a variety of lipids in them (Hildish & Williams, "Chemical Composition of Natural Lipids", Chapman Hall, London, 1964). There is now considerable interest in altering lipid composition by the use of recombinant DNA technology (Knauf, *TIBtech,* February 1987, 40–47), but by no means all of the goals have been realised to date for a variety of reasons, in spite of the ever-increasing sophistication of the technology.

Success in tailoring the lipid content of plant-derived oils requires a firm understanding of the biochemistry and genes involved. Broadly, two approaches are available. First, plants may be modified to permit the synthesis of fatty acids which are new (for the plant); so, for example, laurate and/or stearate may be synthesised in rape. Secondly, the pattern and/or extent of incorporation of fatty acids into the glycerol backbone of the lipid may be altered. It is with this latter approach that the present invention is concerned, although the former approach may additionally be used.

Lipids are formed in plants by the addition of fatty acid moieties onto the glycerol backbone by a series of acyl transferase enzymes. There are three positions on the glycerol molecule at which fatty acid (acyl) moieties may be substituted, and the substitution reached at each position is catalysed by a position-specific enzyme: the enzymes are known as 1-, 2- and 3-acyltransferases, respectively.

One, but not the only, current aim of "lipid engineering" in plants is to provide oils including lipids with a high content of erucic (22:1) acid. Erucic acid-containing lipids are commercially desirable for a number of purposes, particularly as replacements to or supplements for mineral oils in certain circumstances, as alluded to above. In the case of oil seed rape (*Brassica napus*), one of the -most significant oil producing crops in cultivation today, the specificity of the 2-acyltransferase enzyme positively discriminates against the incorporation of erucic acid at position 2. So, even in those cultivars of rape which are able to incorporate erucic acid at positions 1 and 3, where there is no (or at least reduced) discrimination against erucic acid, only a maximum 66% of the fatty acids incorporated into triacyl glycerols can be erucic acid. Such varieties of rape are known as HEAR (high erucic acid rape) varieties.

It would therefore be desirable to increase the erucic acid content of conventional oil seed rape, as well as HEAR varieties; the same can be said of oils of other vegetable oil crops such as maize, sunflower and soya, to name but a few examples. While in principle it may be thought possible to introduce into a desired plant DNA encoding a 2-acyltransferase of different fatty acid specificity, for example from a different plant, in practice there are a number of problems.

First, 2-acyltransferase and 3-acyltransferase are membrane bound, and therefore insoluble, enzymes. They have not been purified. This makes working with them difficult and rules out the use of many conventional DNA cloning procedures. This difficulty does not, paradoxically, lie in the way of cloning the gene (or at least cDNA) encoding the 1-acyltransferase enzyme, which is soluble: in fact, recombinant DNA work has already been undertaken on this enzyme for a completely different purpose, namely the enhancement of chilling resistance in tobacco plant leaves, by Murata et al (*Nature* 356 710–713 is (1992)).

Secondly, very little is known about the 2- and 3-acyltransferases. There is no idea of their size or how they are targeted to membranes. No nucleotide or amino acid sequence data are available and no antibodies have been raised against them.

Although there has been discussion, therefore, of the desirability of modifying 2-acyltransferase specificity, for example by importing a gene coding for the corresponding enzyme, but of different specificity, from another species, there is a pressing need in the art for the key which enables this work to be done.

SUMMARY AND DETAILED DESCRIPTION OF THE INVENTION

The present invention provides such a key, in the form of a DNA sequence (in the specific case, a cDNA sequence) encoding a 2-acyltransferase. The DNA sequence in FIG. 1 (SEQ ID NO: 1) from nucleotides 130 to 1254 encodes the 2-acyltransferase from maize (*Zea mays*), including the stop codon.

According to a first aspect of the invention, therefore, there is provided a recombinant or isolated DNA sequence, preferably encoding an enzyme having membrane-bound acyltransferase activity, and selected from:

(i) a DNA sequence comprising the DNA sequence of FIGS. 1A and 1B (SEQ ID NO: 1) encoding at least from $MET_1$ to $Stop_{375}$ (SEQ ID NO: 2) or its complementary strand, (ii) nucleic acid sequences hybridising to the DNA sequence of FIGS. 1A and 1B (SEQ ID NO: 1), or its complementary strand, under stringent conditions, and (iii) nucleic acid sequences which would hybridise to the DNA sequence of FIGS. 1A and 1B (SEQ ID NO: 1), or its complementary strand, but for the degeneracy of the genetic code.

Fragments of the above DNA sequences, for example of at least 15, 20, 30, 40 or 60 nucleotides in length, are also within the scope of the invention.

Suitable stringent conditions include salt solutions of approximately 0.9 molar at temperatures of from 35° C. to 65° C. More particularly, stringent hybridisation conditions include 6×SSC, 5×Denhardt's solution, 0.5% SDS, 0.5% tetrasodium pyrophosphate and 50 μg/ml denatured herring sperm DNA; washing may be for 2×30 minutes at 65° C. in 1×SSC, 0.1% SDS and 1×30 minutes in 0.2×SSC, 0.1% SDS at 65° C.

Nucleic acid sequences within the scope of the first aspect of the invention will generally encode a protein having 2-acyltransferase activity, as that is the activity of the enzyme encoded by the FIGS. 1A and 1B nucleic acid sequence (SEQ ID NO: 1). Nucleic acid sequences not encoding a protein having enzymic activity (or the relevant enzymic activity) but otherwise conforming to the first aspect of the invention as set out above may be useful for other purposes (and are therefore also encompassed by the invention); for example they may be useful as probes, which is a utility shared by the nucleic acid sequences of the first aspect of the invention, including the FIG. 1 sequence itself.

The probe utility arises as follows. As there is likely to be a high degree of homology between acyltransferases of different species (and particularly between 2-acyltransferases of different species) the FIGS. 1A and 1B sequence (or part of it, or other sequences within the invention) may be used to probe cDNA or genomic libraries of other species in order to clone DNA sequences encoding acyltransferases having desired specificities. For example, if it is desired to produce oil having a high content of erucic acid esterified to glycerol, a DNA library of any species which naturally makes erucic acid may be probed. Suitable plants include meadow foam (Limnanthes spp., especially *L. alba* and, particularly, *L. douglassi)* and Crambe. *Limnanthes douglassi* is the preferred species, as specificity studies show that there is positive discrimination towards incorporation of erucic acid into position 2 of the triacylglyceride. Libraries of organisms other than the higher plants may be probed; for example, certain bacteria may have an acyltransferase of the desired specificity. DNA in accordance with the invention will in general have a higher degree of homology with at least part of the FIGS. 1A and 1B sequence of FIG. 1 (SEQ ID NO: 1) than with known sequences.

Recombinant DNA in accordance with the invention may be in the form of a vector, which may have sufficient regulatory sequences (such as a promoter) to direct expression. Vectors which are not expression vectors are useful for cloning purposes (as expression vectors themselves may be). Host cells (such as bacteria and plant cells) containing vectors in accordance with the invention themselves form part of the invention.

DNA sequences in accordance with the invention can be used in another way in cloning a gene of interest from another species: if the DNA is coupled to a suitable promoter, for example on an expression vector in a suitable host organism, protein may be produced. Such protein may be used to generate polyclonal or monoclonal antibodies, or other binding molecules, which may then be used to screen for expression of homologous proteins in other species, for example as part of a DNA library screening programme.

Suitable cDNA libraries of target species will generally be prepared when the gene of interest is likely to be expressed; so CDNA embryo libraries (prepared at the early lipid synthesis stage), for example of Limnanthes spp. will be preferred.

The invention therefore enables the cloning of a wide variety of genes (or, more generally, DNA sequences encoding acyltransferases, and 2-acyltransferases in particular, using DNA sequences as described above.

Such acyltransferases, such as from Limnanthes spp. may also be cloned directly, for example using complementation studies, from a DNA library of the species in question. For example, if *E. coli* is used as the complementation host, a mutant is chosen which is defective in the relevant enzyme (for example 2-acyltransferase); the DNA library from the target species (such as *L. douglassi*) is cloned into the mutant complementation host; host cells incorporating the target acyltransferase gene in their genome can readily be selected using appropriate selective media. *E. coli* mutant JC201 is a suitable host for use in complementation studies relating to 2-acyltransferase.

Cloning the acyltransferase gene of choice into a microbial host, such as a bacterium like *E. coli,* in such a way that the gene can be expressed has a particularly advantage in that the substrate specificity of the acyltransferase gene can be assessed in the microbial host before transformed plants are prepared, thereby saving considerably on research time. Such an assessment may be made by competitive substrate assays, in which differently detectably labelled candidate substrates for the enzyme compete with each other for incorporation into the glyceride. For example, $^{14}$C-erucyl CoA and $^{3}$H-oleoyl CoA can be used as competitive substrates for 2-acyltransferase, and the relative amounts of $^{14}$C or tritium uptake into glyceride can be measured. (As 2-acyltransferases have acceptor, glycerol-based, substrates and donor, fatty acid-based, substrates, the experiment can be carried out with different acceptors, such as 1-erucyl-glycerol-3-phosphate and 1-oleoyl-glycerol-3-phosphate.) A gene coding for an enzyme which preferentially donates erucic acid to the acceptor (particularly 1-erucyl-glycerol-3-phosphate) may by this means be identified as a DNA sequence of choice for further use in the invention as described below.

In a second aspect of the invention, there is provided a plant having one or more insoluble acyltransferase enzymes having a substrate specificity which differs from the native enzyme of the plant.

While site-directed mutagenesis and/or other protein engineering techniques may be used to alter the specificity of an enzyme native to the plant, it is preferred that the plant be transgenic and incorporate an expressible acyltransferase gene encoding an enzyme of the desired specificity from another species. 2-acyltransferases are the enzymes of choice. For example, as described above, a 2-acyltransferase enzyme which has an enhanced specificity for, or at least no discrimination against, erucic acid, may be made by this means to express in a plant which would not normally incorporate erucic acid into triacylglycerides. An important embodiment of the invention relates to genetically engineered plants which have higher levels of erucic acid incorporated into triacylglycerols than in corresponding non-engineered plants. Preferable though this embodiment may be, though, the invention is not limited to the enhancement of erucic acid incorporation into glycerides: other acids may be desired in other circumstances.

For the acyltransferase transgene to be expressible, a promoter has to be operatively coupled to it. Because at the present state of the art it is difficult precisely too regulate the site of incorporation of a transgene into the host genome, it is preferred that the transgene be coupled to its promoter prior to transformation of the plant. Promoters useful in the invention may be temporal- and/or seed-specific, but there is no need for them to be so: constitutive promoters, such as the CaMV 35S promoter, may be in fact be preferred because they are usually strong promoters. Other tissues are unlikely to be adversely affected if the transgene encoding the acyltransferase enzyme is expressed in them, as the availability of the fatty acid CoA substrates is effectively limited to the seed.

The promoter-transgene construct, once prepared, is introduced into plant cells by any suitable means. The invention extends to such plant cells. Preferably, DNA is transformed into plant cells using a disarmed Ti-plasmid vector and carried by Agrobacterium by procedures known in the art, for example as described in EP-A-0116718 and EP-A-0270822. Alternatively, the foreign DNA could be introduced directly into plant cells using an electrical discharge apparatus. This method is preferred where Agrobacterium is ineffective, for example where the recipient plant is monocotyledonous. Any other method that provides for the stable incorporation of the DNA within the nuclear DNA of any plant cell of any species would also be suitable. This includes species of plant which are not currently capable of genetic transformation.

Preferably DNA in accordance with the invention also contains a second chimeric gene (a "marker" gene) that enables a transformed plant or tissue culture containing the foreign DNA to be easily distinguished from other plants or tissue culture that do not contain the foreign DNA. Examples of such a marker gene include antibiotic resistance (Herrera-Estrella et al, *EMBO J.* 2(6) 987–95 (1983) and Herrera-Estrella et al, *Nature* 303 209–13 (1983)), herbicide resistance (EP-A-0242246) and glucuronidase (GUS) expression (EP-A-0344029). Expression of the marker gene is preferably controlled by a second promoter which allows expression in cells other than the tapetum, thus allowing selection of cells or tissue containing the marker at any stage of regeneration of the plant. The preferred second promoter is derived from the gene which encodes the 35S subunit of Cauliflower Mosaic Virus (CaMV) coat protein. However any other suitable second promoter could be used.

A whole plant can be regenerated from a single transformed plant cell, and the invention therefore provides transgenic plants (or parts of them, such as propagating material) including DNA in accordance with the invention as described above. The regeneration can proceed by known methods.

In one embodiment of the invention, the transgenic plant's native acyltransferase gene which corresponds to the transgene may be rendered at least partially inoperative or removed. So, if the transgene encodes a 2-acyltransferase, the plant's native 2-acyltransferase may be rendered inoperative by, for example, antisense or ribozyme techniques, as is known in the art.

By means of the invention, plants generating oil with a tailored lipid content may be produced. For example, the lipid composition of triacylglycerides in a plant may be substantially altered to produce triacylglycerides with a desired fatty acid (for example erucic acid) content higher than has hitherto been possible. For example, oil seed rape (*B. napus*) may be transformed to produce oil whose triacylglyceride has an erucic acid content of over 70%.

It can readily be seen that plants with increased lipid levels may be produced by means of the invention. However, the invention is also useful for producing plants with decreased lipid levels, which may be desired if elevated protein and/or starch levels are required. Decreased lipid levels may be achieved by interfering with the proper functioning of a gene encoding a 2-acyltransferase, for example by antisense or ribozyme technology. (Such reduced-lipid plants may if desired be further engineered for higher protein and/or starch content, if wished.)

Promoters which naturally drive 2-acyltransferases may also be obtained by hybridisation and/or restriction and/or sequencing studies using the FIGS. 1A and 1B sequence.

The invention enables the production of protein encoded by DNA of the first aspect of the invention, should that be desired. The protein may be expressed by host cells harbouring DNA in the form of an expression vector. The protein, which may be an enzyme having 2-acyltransferase activity, may have an amino acid sequence which is identical to or homologous with the FIGS. 1A and 1B sequence (SEQ ID NO: 2). The degree of homology will generally be greater than that of known proteins, and may be at least 40, 50, 60, 70, 80, 90, 95 or 99%.

Preferred features of each aspect of the invention are as for each other aspect mutatis mutandis.

BRIEF DESCRIPTION OF THE DRAWINGS

The invention is illustrated by the following examples. The examples refer to the accompanying drawings, in which:

FIGS. 1A and 1B shows the cDNA sequence derived in Example 1 (SEQ ID NO: 1) and its derived protein sequence (SEQ ID NO: 2).

FIG. 2 shows a sequence alignment of part of the gene products of plsB (SEQ ID NO: 3) and plsC (SEQ ID NO: 4) with part of the sequence shown in FIG. 1 (SEQ ID NO: 5), showing a conserved motif. plsB is the *E. coli* sn-glycerol-3-phosphate acyltransferase gene and plsC the 1-acyl-sn-glycerol-3-phosphate acyltransferease gene of *E. coli.* Double points indicate exact matches between two sequences and a single point conservative amino acid substitutions. Stars indicate identical amino acids in all three sequences and residues conserved in two out of the three sequences are marked by a + symbol.

(FIG. 3B): JC201 containing the plasmid pPLSC, which encodes the *E. coli* 1-acyl-sn-glycerol-3-phosphate acyltransferase gene; (FIG. 3C): JC201 containing the plasmid whose CDNA insert sequence is shown in FIGS. 1A and 1B. LPA, lysophosphatidic acid; PE, phosphatidylethanolamine; CL, cardiolipin; PG, phosphatidylglycerol; PA, phosphatidic acid; O origin. 20% of the $^{32}$p is incorporated in LPA in JC201 and all of the corresponding label is incorporated in PE in both of the other two strains.

FIGS. 5A and 5B shows a comparison of the protein sequence shown in FIGS. 1A and 1B (SEQ ID NO: 6) with that derived (SEQ ID NO: 7) from a *B. napus* seed cDNA insert which was isolated by DNA hybridisation to the maize cDNA sequence. The sequences were aligned with the FastA align program (1988). Double points signify identical amino acids and single points conservative amino acid substitutions.

Maize=374 aa vs.rape=311 aa 51.5% identity; Optimised score: 705

EXAMPLE 1

Derivation of the FIG. 1 cDNA Sequence

Complementation studies using a maize cDNA expression library transferred into the *E. coli* mutant JC201 allowed the isolation of a plasmid encoding a 2-acyltransferase enzyme from maize. The cDNA insert of this plasmid is 1.6kb in size, and includes a poly A tail of 70 bp. The insert was sequenced to give the data shown and translation of the sequence revealed the present of only one large open reading frame. This is shown on FIGS. 1A and 1B with proposed start methionine and stop codon boxed. The 2-acyltransferase is 374 amino acids in size and sequencing upstream of open reading frame showed that the protein is expressed as part of a fusion protein in *E. coli.* This consists of 10 amino acids of the β-galactosidase protein, 43 amino acids (shown in sequence) corresponding to the 5' untranslated region of the mRNA and the 374 amino acid protein. Protein sequence comparisons of the large open reading frame with the 2-acyltransferase of *E. coli* show little overall identity but there is a stretch of 80 residues which has a high level of conservative substitution and contains some amino acids that are conserved in the 2-acyltransferase, 1-acyltransferase and N-acetyl glucosamirie acyltransferase of *E. coli.*

EXAMPLE 2

Incorporation of 32p into Total Phospholipids *E. coli* strains were grown in minimal medium containing $^{32}$p orthophosphate. Total glycerolipids were extracted into organic solvents and separated by 2D thin layer chromatography (FIGS. 3A–C) (Lysophosphatidic acid (LPA) is the substrate for 2-acyltransferase (2-AT)).

Figure 3A:
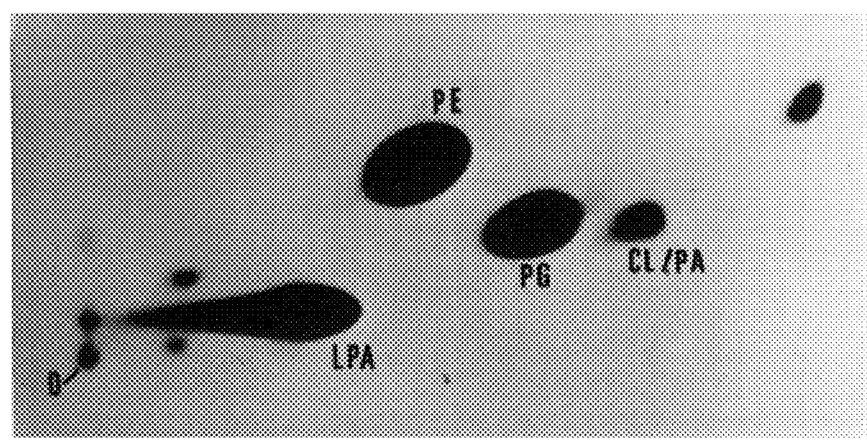
FIGS. 3A, 3B and 3C: Membrane phospholipids from *E. coldi* strains were extracted into chloroform and separated by 2-dimensional thin layer chromatography. The first dimension (ascending) was developed using chloroform-:methanol:water (65:25:4) and the second dimension (left to right) developed. with chloroform:methanol:acetic acid (65:25:10). Phospholipids were visualised by autoradiography for 16 hours at −70° C. using Fuji RX film. The *E. coli* strains used were (FIG. 3A): JC201 which carries a thermosensitive mutation in the 1-acyl-sn-glycerol-3-phosphate acyltransferase gene.
Figure 3B:
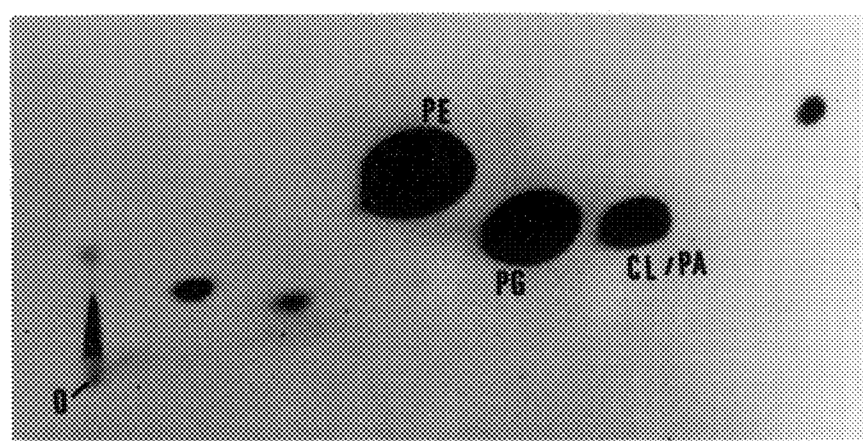
Figure 3C:
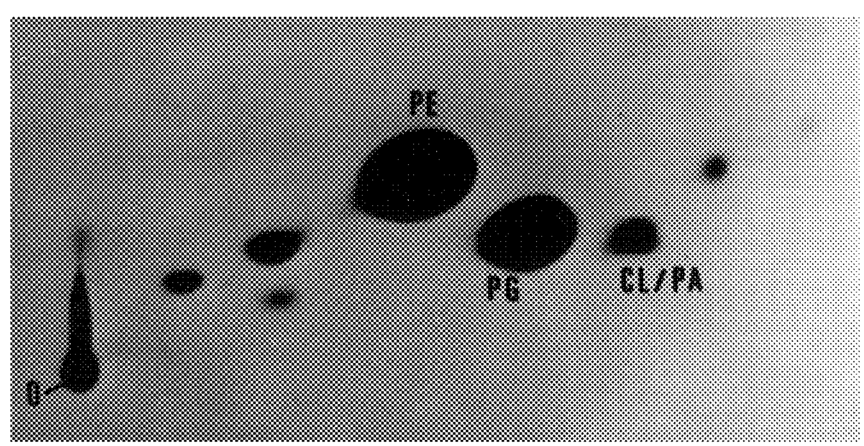

As can be seen in FIG. 3A, the accumulation of $^{32}$P-labelled LPA in the mutant JC 201 illustrates the absence of a fully functional 2-AT. Addition of a plasmid carrying either the native *E. coli* gene (FIG. 3B), or the maize clone given in FIG. 1 (FIG. 3C) restores 2-AT activity to the cells, allowing LPA to be removed and further metabolised. (Lysophosphatidic acid.)

These data indicate that the DNA sequence given in FIGS. 1A and 1B codes for 2-AT.

EXAMPLE 3

Over expression of the cDNA

The cDNA region specifying the protein sequence given in FIGS. 1A and 1B was cloned into the *E. coli* overexpression vector pET11d (Studier et al, Meth. Enzymol. 185 60–89 (1990)). Increased 2-acyltransferase activity following induction of expression from the plasmid insert confirmed that the sequence in FIGS. 1A and 1B is that of 2-AT.

EXAMPLE 4

Figure 4:
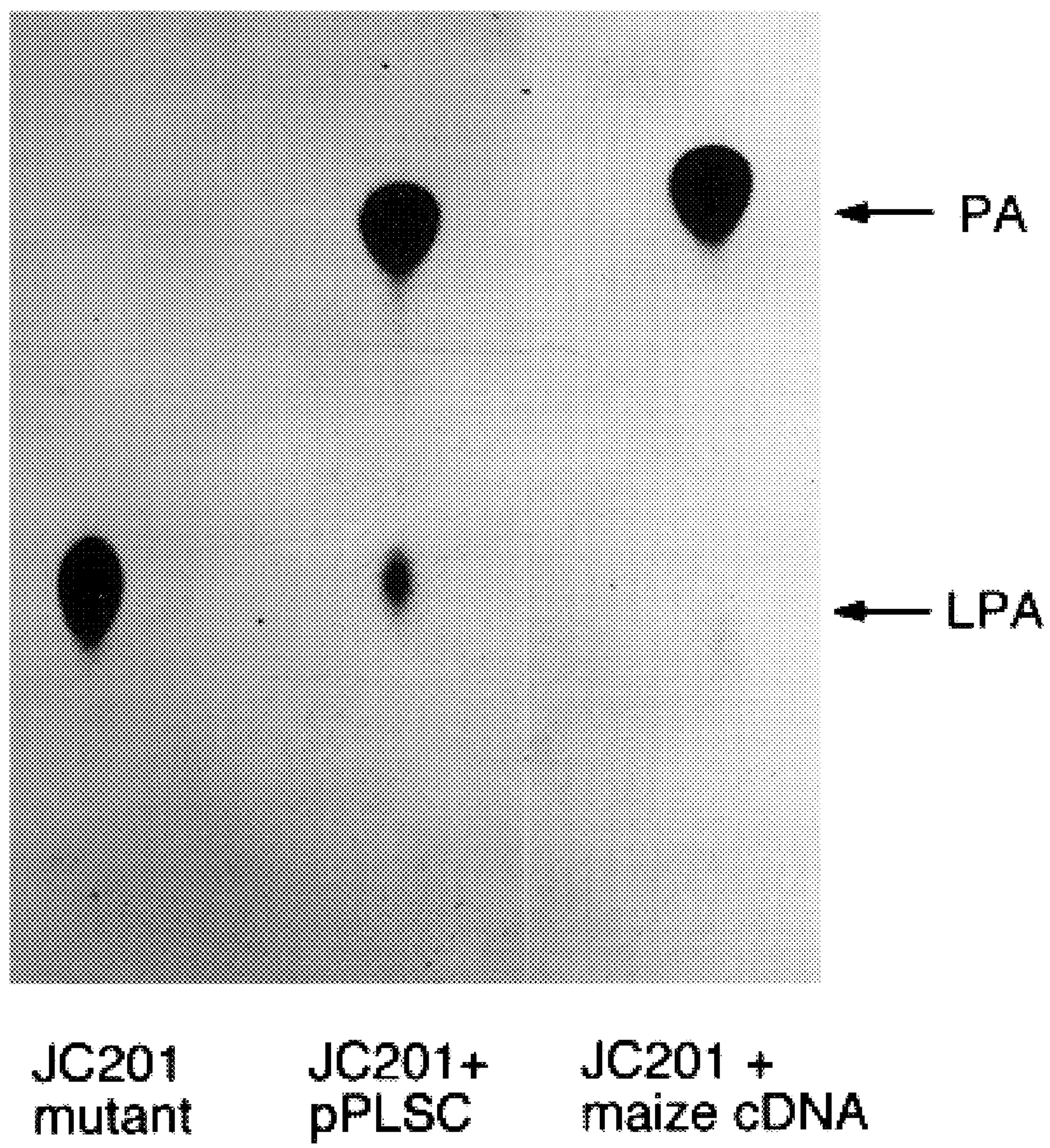
FIG. 4: Acyltransferase assays were performed using $^{32}$P-labelled lysophosphatidic acid which had been extracted from the *E. coli* strain JC201 and oleoyl CoA as an acyl donor. Phospholipids present in the reaction mixtures were extracted into chloroform and separated using silica gel thin layer chromatography. Chloroform:methanol: acetic acid-:water (25:15:4:2) was used to develop the plates. The phospholipids were visualised by autoradiography for 16 hours at −70° C. using Fuji RX film. The *E. coli* strains used were: JC201 which carries a thermosensitive mutation in the 1-acyl-sn-glycerol-3-phosphate acyltransferase gene; JC201 containing the plasmid pPLSC which encodes the *E. coli* 1-acyl-sn-glycerol-3-phosphate acyltransferase gene; JC201 containing the plasmid whose maize cDNA insert sequence is shown in FIGS. 1A and 1B. LPA, lysophosphatidic acid; PA, phosphatidic acid.

Localisation of 2-AT activity in *E. coli* cells containing the maize clone 2-acyltransferase assays were carried out using membranes isolated from the mutant strain JC.201 which lacks 2-AT and from JC.201 containing the maize plasmid (FIG. 4). 2-AT activity was not detected in membrane fractions from JC.201. The addition of a plasmid carrying the native *E. coli* gene or the sequence given in FIGS. 1A and 1B (SEQ ID NO: 1), to JC.201 resulted in restoration of 2-AT activity to the membranes.

EXAMPLE 5

Using the Maize cDNA as a Heterologous Probe to Obtain cDNA from Oilseed Rape A seed cDNA library from *Brassica napus* was screened with the sequence given in FIGS. 1A and 1B (SEQ ID NO: 1), using standard techniques (Sambrook et al "Molecular Cloning—A Laboratory Manual", 2nd Edition, Cold Spring Harbor Laboratory Press, 1989).

Conditions

For the hybridisation of the maize CDNA insert to the rape library: hybridisation was in 6×SSC, 5×Denhardts solution, 0.5%SDS, 0.5% tetrasodium pyrophosphate and 50 ugml$^{-1}$ denatured herring sperm DNA. The filters were washed 2×30 minutes at 65° C. in 1×SSC, 0.1%SDS and 1×30 minutes in 0.2×SSC, 0.1%SDS at 65° C.

A hybridising clone was sequenced and a protein sequence derived for the large ORF. Alignment of this protein sequence with that derived from the maize cDNA clone given in FIGS. 1A and 1B (SEQ ID NO: 1), is shown in FIGS. 5A and 5B.

The strong identity between these sequences illustrates the potential of using the sequence given in FIGS. 1A and 1B (SEQ ID NO: 1) obtain other 2-ATS.

EXAMPLE 6

Tranegenic Plants

The sequence given in FIGS. 1A and 1B (SEQ ID NO: 1) can be cloned, alongside a suitable promoter, into a suitable vector for expression in plants. The vector can be used to transform plants and the resulting plants expressing the 2-AT can be analysed for lipid content. Lipid metabolism is expected to be upregulated and elevated lipid levels were detectable in seeds.

EXAMPLE 7

Antisense

The sequence given in FIGS. 1A and 1B (SEQ ID NO: 1) may be cloned, alongside a suitable promoter, in the antisense orientation into a suitable vector for expression in plants. The vector can be used to transform plants and the resulting plants expressing the 2-AT can be analysed for protein and starch content. Elevated levels of starch and protein are expected to be detectable in seeds.

EXAMPLE 8

Down-Regulation of Native 2-AT

The DNA sequence of a 2-AT derived from *L. douglassii* (obtained as described in Example 5) can be introduced into oilseed rape (OSR) under the expression of a suitable promoter, using vectors and plant transformation methods well known in the art. A second sequence, comprising antisense or ribozymes against the rape cDNA (Example 5) can be introduced for simultaneous expression. The resultant transformed plant is expected to have 2-AT activity corresponding to that of *L. douglassii,* with concurrent down regulation of the native rape 2-AT gene.

The modified OSR plant thus obtained had higher levels of erucic acid in position 2 of its triacylglycerols than wild type plants. In addition higher levels of trierucin are found in the seed oil.

EXAMPLE 9

Genomic Library Screening

The sequence given in FIGS. 1A and 1B (SEQ ID NO: 1) is used to screen a genomic library of Arabidopsis and a hybrid using clone obtained. Using standard techniques, a promoter may be derived from this clone. The promoter may be used to drive expression in plant cell membranes.

What is claimed is:

1. A plant having at least one insoluble foreign acyltransferase, said acyltransferase having a substrate specificity which differs from the native acyltransferase of said plant.

2. The plant according to claim 1, said plant being transgenic for an insoluble acyltransferase from another species.

3. The plant according to claim 1 or 2, said plant being selected from the group consisting of rape, maize, sunflower and soya.

4. The plant according to claim 2, wherein the said other species is a species of a genus selected from the group consisting of Limnanthes and Crambe.

5. The plant according to claim 1, wherein said insoluble foreign acyltransferase is 2-acyltransferase.

6. The plant according to claim 5, wherein said foreign 2-acyltransferase has a higher specificity for erucic acid than the native 2-acyltransferase of said plant.

7. The plant according to claim 6, wherein said native 2-acyltransferase is rendered at least partially inoperative.

8. The plant according to claim 4, wherein said other species is selected fi-om the group consisting of *L. alba* and *L. douglassi.*

9. The plant according to claim 8, wherein said other species is *L. douglossi.*

10. The plant according to claim 2, wherein said acyltransferase from another species is encoded by anucleic acid that hybridizes, under stringent conditions, to the complement of the DNA sequence of SEQ ID No. 1.

11. The plant according to claim 10, wherein said acyltransferase from another species is encoded by the coding sequence of SEQ ID No.1.

12. The plant according to claim 5, wherein the amino acid sequence of said 2-acyltransferase comprises amino acid about 1 to about 374 of SEQ ID No. 2.

13. The plant according to claim 6, wherein said native acyltransferase is removed.

14. Seeds derived from the plant of claim 2.

15. Oil derived from the seeds of claim 14.

16. The oil according to claim 15, wherein the erucic acid content of said oil is over 70%.

17. A method of generating oil, comprising:

(a) cultivating a plant according to any one of claims 1, 2, 5, 10, 11 or 12; and (b) harvesting oil produced by said plant or by a part thereof.

18. A method of making the plant of claim 2, comprising: introducing into a plant a transgene encoding an acyltransferase from another species.

19. The method according to claim 18, said plant being selected from the group consisting of rape, maize, sunflower and soya.

20. The method according to claim 18, wherein said acyltransferase is 2-acyltransferase.

21. The method according to claim 18, wherein said acyltransferase from another species is encoded by a nucleic acid that hybridizes, under stringent conditions, to the complement of the DNA sequence of SEQ ID No. 1.

22. The plant according to claim 21, wherein said acyltransferase from another species is encoded by the coding sequence of SEQ ID No. 1.

23. The plant obtained by the method of claim 18.

24. A method of making a transgenic plant, comprising: regenerating a plant from a single cell of the plant of claim 2.

25. The plant according to claim 2, wherein said insoluble acyltransferase is 2-acyltransferase.

26. The plant according to claim 25, wherein the amino acid sequence of said 2-acyltransferase comprises amino acid about 1 to about 374 of SEQ ID No.2.

27. The plant according to claim 25, wherein said 2-acyltransferase has a higher specificity for a erucic acid than the native 2-acyltransferase of said plant.

28. The plant according to claim 25, wherein the native 2-acyltransferase is at least partially inoperative.

29. The plant according to claim 25, wherein the native 2-acyltransferase is removed.

30. The plant according to claim 1, wherein said foreign acyltransferase is encoded by a nucleic acid that hybridizes, under stringent conditions, to the complement ofthe DNA sequence of SEQ ID No.1.

31. The plant according to claim 30, wherein said foreign acyltransferase is encoded by the coding sequence of SEQ ID No.1.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
(A) LENGTH: 1514 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 130..1254

(xi) SEQUENCE DESCRIPTION: SEQ ID NO: 1:

```
CCCCGTCCTC CTCGTCGCCG GCGGAGCCGC CTACTATCGC CTGGAGAAGG AGCGCCGCGG     60

GGAGCTTTTC CCACTGCCGA CTGCCGTCTG ACCCTCCGAG ATCGGAAGCG GCGCCGGCGC    120

CGGCCGGCG ATG GCG ATC CCG CTC GTG CTC GTC GTG CTC CCG CTC GGC        168
          Met Ala Ile Pro Leu Val Leu Val Val Leu Pro Leu Gly
            1               5                  10

CTG CTC TTC CTC CTG TCC GGC CTC ATC GTC AAC GCC ATC CAG GCC GTC      216
Leu Leu Phe Leu Leu Ser Gly Leu Ile Val Asn Ala Ile Gln Ala Val
     15                  20                  25

CTA TTT GTG ACG ATA AGG CCC TTT TCG AAG AGC TTC TAC CGT CGG ATC      264
Leu Phe Val Thr Ile Arg Pro Phe Ser Lys Ser Phe Tyr Arg Arg Ile
 30                  35                  40                  45

AAC AGA TTC TTG GCC GAG CTG CTG TGG CTT CAG CTT GTC TGG GTG GTG      312
Asn Arg Phe Leu Ala Glu Leu Leu Trp Leu Gln Leu Val Trp Val Val
                 50                  55                  60

GAC TGG TGG GCA GGT GTT AAG GTA CAA CTG CAT GCA GAT GAG GAA ACT      360
Asp Trp Trp Ala Gly Val Lys Val Gln Leu His Ala Asp Glu Glu Thr
             65                  70                  75

TAC AGA TCA ATG GGT AAA GAG CAT GCA CTC ATC ATA TCA AAT CAT CGG      408
Tyr Arg Ser Met Gly Lys Glu His Ala Leu Ile Ile Ser Asn His Arg
         80                  85                  90

AGT GAT ATT GAT TGG CTC ATT GGA TGG ATA TTG GCC CAG CGT TCA GGG      456
Ser Asp Ile Asp Trp Leu Ile Gly Trp Ile Leu Ala Gln Arg Ser Gly
     95                 100                 105

TGC CTT GGA AGT ACA CTT GCT GTC ATG AAG AAG TCA TCC AAG TTC CTT      504
Cys Leu Gly Ser Thr Leu Ala Val Met Lys Lys Ser Ser Lys Phe Leu
110                 115                 120                 125

CCA GTT ATT GGC TGG TCA ATG TGG TTT GCA GAG TAC CTC TTT TTG GAA      552
Pro Val Ile Gly Trp Ser Met Trp Phe Ala Glu Tyr Leu Phe Leu Glu
                130                 135                 140

AGG AGC TGG GCC AAG GAT GAA AAG ACA CTA AAG TGG GGT CTC CAA AGG      600
Arg Ser Trp Ala Lys Asp Glu Lys Thr Leu Lys Trp Gly Leu Gln Arg
            145                 150                 155

TTG AAA GAC TTC CCT AGA CCA TTT TGG CTA GCT CTT TTC GTC GAG GGT      648
Leu Lys Asp Phe Pro Arg Pro Phe Trp Leu Ala Leu Phe Val Glu Gly
        160                 165                 170

ACT CGC TTT ACT CCA GCA AAG CTT CTC GCA GCT CAG GAA TAT GCG GCC      696
Thr Arg Phe Thr Pro Ala Lys Leu Leu Ala Ala Gln Glu Tyr Ala Ala
    175                 180                 185

TCC CAG GGC TTA CCG GCT CCT AGA AAT GTA CTT ATT CCA CGT ACC AAG      744
Ser Gln Gly Leu Pro Ala Pro Arg Asn Val Leu Ile Pro Arg Thr Lys
190                 195                 200                 205
```

-continued

```
GGA TTT GTA TCT GCT GTA AGT ATT ATG CGA GAT TTT GTT CCA GCC ATT       792
Gly Phe Val Ser Ala Val Ser Ile Met Arg Asp Phe Val Pro Ala Ile
                210                 215                 220

TAT GAT ACA ACT GTA ATA GTC CCT AAA GAT TCC CCT CAA CCA ACA ATG       840
Tyr Asp Thr Thr Val Ile Val Pro Lys Asp Ser Pro Gln Pro Thr Met
            225                 230                 235

CTG CGG ATT TTG AAA GGG CAA TCA TCA GTG ATA CAT GTC CGC ATG AAA       888
Leu Arg Ile Leu Lys Gly Gln Ser Ser Val Ile His Val Arg Met Lys
        240                 245                 250

CGT CAT GCA ATG AGT GAG ATG CCA AAA TCA GAT GAG GAT GTT TCA AAA       936
Arg His Ala Met Ser Glu Met Pro Lys Ser Asp Glu Asp Val Ser Lys
    255                 260                 265

TGG TGT AAA GAC ATT TTT GTG GCA AAG GAT GCC TTA CTG GAC AAG CAT       984
Trp Cys Lys Asp Ile Phe Val Ala Lys Asp Ala Leu Leu Asp Lys His
270                 275                 280                 285

TTG GCA ACA GGC ACT TTC GAT GAG GAG ATT AGA CCT ATT GGC CGT CCA      1032
Leu Ala Thr Gly Thr Phe Asp Glu Glu Ile Arg Pro Ile Gly Arg Pro
                290                 295                 300

GTG AAA TCA TTG CTG GTG ACC CTG TTC TGG TCG TGC CTC CTG CTG TTT      1080
Val Lys Ser Leu Leu Val Thr Leu Phe Trp Ser Cys Leu Leu Leu Phe
            305                 310                 315

GGC GCC ATC GAG TTC TTC AAG TGG ACA CAG CTT CTG TCG ACG TGG AGG      1128
Gly Ala Ile Glu Phe Phe Lys Trp Thr Gln Leu Leu Ser Thr Trp Arg
        320                 325                 330

GGT GTG GCG TTC ACT GCC GCA GGG ATG GCG CTT GTG ACG GGT GTC ATG      1176
Gly Val Ala Phe Thr Ala Ala Gly Met Ala Leu Val Thr Gly Val Met
    335                 340                 345

CAT GTC TTC ATC ATG TTC TCC CAG GCT GAG CGG TCG AGC TCA GCC AGG      1224
His Val Phe Ile Met Phe Ser Gln Ala Glu Arg Ser Ser Ser Ala Arg
350                 355                 360                 365

GCG GCA CGG AAC CGG GTC AAG AAG GAA TGAAAAATGG AGGGTGGAGA            1271
Ala Ala Arg Asn Arg Val Lys Lys Glu
                370                 375

TGAGGTTCTC GTGGGGTTTG TTATGGGCAA CCTTCAAAAG GACTCTCCAT TCATATTAGT   1331

ATTAATTCAT ATATATGCAG CGCCAAATTC CAGACATTGA TATGCTCTCA AATAGGATGT   1391

TCTGCTCCCC TCTTGTATTT GTATGCAGGA AAGGGTTTGT AGGGAGTTTA CCCCCCCCCC   1451

CCCCCCCCCC GCCTTTCTTT GGGGAAGAAA GACATATTCT GGAAGCCTTC CAGTAGTTCA   1511

AAA                                                                  1514
```

(2) INFORMATION FOR SEQ ID NO: 2:

(i) SEQUENCE CHARACTERISTICS:
(A) LENGTH: 374 amino acids
(B) TYPE: amino acid
(D) TOPOLOGY: linear (ii) MOLECULE TYPE: protein (xi) SEQUENCE DESCRIPTION: SEQ ID NO: 2:

```
Met Ala Ile Pro Leu Val Leu Val Val Leu Pro Leu Gly Leu Leu Phe
  1               5                  10                  15

Leu Leu Ser Gly Leu Ile Val Asn Ala Ile Gln Ala Val Leu Phe Val
             20                  25                  30

Thr Ile Arg Pro Phe Ser Lys Ser Phe Tyr Arg Arg Ile Asn Arg Phe
        35                  40                  45

Leu Ala Glu Leu Leu Trp Leu Gln Leu Val Trp Val Val Asp Trp Trp
     50                  55                  60
```

-continued

```
Ala Gly Val Lys Val Gln Leu His Ala Asp Glu Glu Thr Tyr Arg Ser
 65                  70                  75                  80

Met Gly Lys Glu His Ala Leu Ile Ile Ser Asn His Arg Ser Asp Ile
                85                  90                  95

Asp Trp Leu Ile Gly Trp Ile Leu Ala Gln Arg Ser Gly Cys Leu Gly
            100                 105                 110

Ser Thr Leu Ala Val Met Lys Lys Ser Ser Lys Phe Leu Pro Val Ile
        115                 120                 125

Gly Trp Ser Met Trp Phe Ala Glu Tyr Leu Phe Leu Glu Arg Ser Trp
    130                 135                 140

Ala Lys Asp Glu Lys Thr Leu Lys Trp Gly Leu Gln Arg Leu Lys Asp
145                 150                 155                 160

Phe Pro Arg Pro Phe Trp Leu Ala Leu Phe Val Glu Gly Thr Arg Phe
                165                 170                 175

Thr Pro Ala Lys Leu Leu Ala Ala Gln Glu Tyr Ala Ala Ser Gln Gly
            180                 185                 190

Leu Pro Ala Pro Arg Asn Val Leu Ile Pro Arg Thr Lys Gly Phe Val
        195                 200                 205

Ser Ala Val Ser Ile Met Arg Asp Phe Val Pro Ala Ile Tyr Asp Thr
    210                 215                 220

Thr Val Ile Val Pro Lys Asp Ser Pro Gln Pro Thr Met Leu Arg Ile
225                 230                 235                 240

Leu Lys Gly Gln Ser Ser Val Ile His Val Arg Met Lys Arg His Ala
                245                 250                 255

Met Ser Glu Met Pro Lys Ser Asp Glu Asp Val Ser Lys Trp Cys Lys
            260                 265                 270

Asp Ile Phe Val Ala Lys Asp Ala Leu Leu Asp Lys His Leu Ala Thr
        275                 280                 285

Gly Thr Phe Asp Glu Glu Ile Arg Pro Ile Gly Arg Pro Val Lys Ser
    290                 295                 300

Leu Leu Val Thr Leu Phe Trp Ser Cys Leu Leu Leu Phe Gly Ala Ile
305                 310                 315                 320

Glu Phe Phe Lys Trp Thr Gln Leu Leu Ser Thr Trp Arg Gly Val Ala
                325                 330                 335

Phe Thr Ala Ala Gly Met Ala Leu Val Thr Gly Val Met His Val Phe
            340                 345                 350

Ile Met Phe Ser Gln Ala Glu Arg Ser Ser Ser Ala Arg Ala Ala Arg
        355                 360                 365

Asn Arg Val Lys Lys Glu
    370
```

(2) INFORMATION FOR SEQ ID NO: 3:

(i) SEQUENCE CHARACTERISTICS:
(A) LENGTH: 15 amino acids
(B) TYPE: amino acid
(D) TOPOLOGY: linear (ii) MOLECULE TYPE: protein (xi) SEQUENCE DESCRIPTION: SEQ ID NO: 3:

```
Tyr Phe Val Glu Gly Gly Arg Ser Arg Thr Gly Arg Leu Leu Asp
1               5                   10                  15
```

(2) INFORMATION FOR SEQ ID NO: 4:

(i) SEQUENCE CHARACTERISTICS:

-continued (A) LENGTH: 15 amino acids
(B) TYPE: amino acid
(D) TOPOLOGY: linear (ii) MOLECULE TYPE: protein (xi) SEQUENCE DESCRIPTION: SEQ ID NO: 4:

```
Met Phe Pro Glu Gly Thr Arg Ser Arg Gly Arg Gly Leu Leu Pro
1               5                   10                  15
```

(2) INFORMATION FOR SEQ ID NO: 5:

(i) SEQUENCE CHARACTERISTICS:
(A) LENGTH: 15 amino acids
(B) TYPE: amino acid
(D) TOPOLOGY: linear (ii) MOLECULE TYPE: protein (xi) SEQUENCE DESCRIPTION: SEQ ID NO: 5:

```
Leu Phe Val Glu Gly Thr Arg Phe Thr Pro Ala Lys Leu Leu Ala
1               5                   10                  15
```

(2) INFORMATION FOR SEQ ID NO: 6:

(i) SEQUENCE CHARACTERISTICS:
(A) LENGTH: 374 amino acids
(B) TYPE: amino acid
(D) TOPOLOGY: linear (ii) MOLECULE TYPE: protein (xi) SEQUENCE DESCRIPTION: SEQ ID NO: 6:

```
Met Ala Ile Pro Leu Val Leu Val Val Leu Pro Leu Gly Leu Leu Phe
1               5                   10                  15

Leu Leu Ser Gly Leu Ile Val Asn Ala Ile Gln Ala Val Leu Phe Val
            20                  25                  30

Thr Ile Arg Pro Phe Ser Lys Ser Phe Tyr Arg Arg Ile Asn Arg Phe
        35                  40                  45

Leu Ala Glu Leu Leu Trp Leu Gln Leu Val Trp Val Val Asp Trp Trp
    50                  55                  60

Ala Gly Val Lys Val Gln Leu His Ala Asp Glu Glu Thr Tyr Arg Ser
65                  70                  75                  80

Met Gly Lys Glu His Ala Leu Ile Ile Ser Asn His Arg Ser Asp Ile
                85                  90                  95

Asp Trp Leu Ile Gly Trp Ile Leu Ala Gln Arg Ser Gly Cys Leu Gly
            100                 105                 110

Ser Thr Leu Ala Val Met Lys Lys Ser Ser Lys Phe Leu Pro Val Ile
        115                 120                 125

Gly Trp Ser Met Trp Phe Ala Glu Tyr Leu Phe Leu Glu Arg Ser Trp
    130                 135                 140

Ala Lys Asp Glu Lys Thr Leu Lys Trp Gly Leu Gln Arg Leu Lys Asp
145                 150                 155                 160

Phe Pro Arg Pro Phe Trp Leu Ala Leu Phe Val Glu Gly Thr Arg Phe
                165                 170                 175

Thr Pro Ala Lys Leu Leu Ala Ala Gln Glu Tyr Ala Ala Ser Gln Gly
            180                 185                 190

Leu Pro Ala Pro Arg Asn Val Leu Ile Pro Arg Thr Lys Gly Phe Val
        195                 200                 205

Ser Ala Val Ser Ile Met Arg Asp Phe Val Pro Ala Ile Tyr Asp Thr
    210                 215                 220
```

```
Thr Val Ile Val Pro Lys Asp Ser Pro Gln Pro Thr Met Leu Arg Ile
225                 230                 235                 240

Leu Lys Gly Gln Ser Ser Val Ile His Val Arg Met Lys Arg His Ala
                245                 250                 255

Met Ser Glu Met Pro Lys Ser Asp Glu Asp Val Ser Lys Trp Cys Lys
            260                 265                 270

Asp Ile Phe Val Ala Lys Asp Ala Leu Leu Asp Lys His Leu Ala Thr
        275                 280                 285

Gly Thr Phe Asp Glu Glu Ile Arg Pro Ile Gly Arg Pro Val Lys Ser
    290                 295                 300

Leu Leu Val Thr Leu Phe Trp Ser Cys Leu Leu Leu Phe Gly Ala Ile
305                 310                 315                 320

Glu Phe Phe Lys Trp Thr Gln Leu Leu Ser Thr Trp Arg Gly Val Ala
                325                 330                 335

Phe Thr Ala Ala Gly Met Ala Leu Val Thr Gly Val Met His Val Phe
            340                 345                 350

Ile Met Phe Ser Gln Ala Glu Arg Ser Ser Ser Ala Arg Ala Ala Arg
        355                 360                 365

Asn Arg Val Lys Lys Glu
    370
```

(2) INFORMATION FOR SEQ ID NO: 7:

(i) SEQUENCE CHARACTERISTICS:
(A) LENGTH: 295 amino acids
(B) TYPE: amino acid
(D) TOPOLOGY: linear (ii) MOLECULE TYPE: protein (xi) SEQUENCE DESCRIPTION: SEQ ID NO: 7:

```
Met Ala Met Ala Ala Ala Val Ile Val Pro Leu Gly Ile Leu Phe Phe
1               5                   10                  15

Ile Ser Gly Leu Val Val Asn Leu Leu Gln Arg Ser Gly Cys Leu Gly
            20                  25                  30

Ser Ala Leu Ala Val Met Lys Lys Ser Ser Lys Phe Leu Pro Val Ile
        35                  40                  45

Gly Trp Ser Met Trp Phe Ser Glu Tyr Leu Phe Leu Glu Arg Asn Trp
    50                  55                  60

Ala Lys Asp Glu Ser Thr Leu Lys Ser Gly Leu Gln Arg Leu Asn Asp
65                  70                  75                  80

Phe Pro Arg Pro Phe Trp Leu Ala Leu Phe Val Glu Gly Thr Arg Phe
                85                  90                  95

Thr Glu Ala Lys Leu Lys Ala Ala Gln Glu Tyr Ala Ala Ser Ser Glu
            100                 105                 110

Leu Pro Val Pro Arg Asn Val Leu Ile Pro Arg Thr Lys Gly Phe Val
        115                 120                 125

Ser Ala Val Ser Asn Met Arg Ser Phe Val Pro Ala Ile Tyr Asp Met
    130                 135                 140

Thr Val Ala Ile Pro Lys Thr Ser Pro Pro Pro Thr Met Leu Arg Leu
145                 150                 155                 160

Phe Lys Gly Gln Pro Ser Val Val His Val His Ile Lys Cys His Ser
                165                 170                 175

Met Lys Asp Leu Pro Glu Ser Glu Asp Glu Ile Ala Gln Trp Cys Arg
            180                 185                 190
```

-continued

```
Asp Gln Phe Val Thr Lys Asp Ala Leu Leu Asp Lys His Ile Ala Ala
        195                 200                 205

Asp Thr Phe Ala Gly Gln Lys Glu Gln Asn Ile Gly Arg Pro Ile Lys
    210                 215                 220

Ser Leu Ala Val Val Leu Ser Trp Ala Cys Leu Leu Thr Leu Gly Ala
225                 230                 235                 240

Met Lys Phe Leu His Trp Ser Asn Leu Phe Ser Ser Trp Lys Gly Ile
                245                 250                 255

Ala Leu Ser Ala Leu Gly Leu Gly Ile Ile Thr Leu Cys Met Gln Ile
            260                 265                 270

Leu Ile Arg Ser Ser Gln Ser Glu Arg Ser Thr Pro Ala Lys Val Ala
        275                 280                 285

Pro Ala Lys Pro Lys Asp Asn
    290                 295
```